(12) United States Patent
Takizawa et al.

(10) Patent No.: US 8,594,766 B2
(45) Date of Patent: Nov. 26, 2013

(54) MAGNETIC RESONANCE IMAGING APPARATUS AND METHOD

(75) Inventors: Masahiro Takizawa, Tokyo (JP); Tetsuhiko Takahashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1149 days.

(21) Appl. No.: 12/278,237

(22) PCT Filed: Feb. 1, 2007

(86) PCT No.: PCT/JP2007/051706
§ 371 (c)(1),
(2), (4) Date: Aug. 4, 2008

(87) PCT Pub. No.: WO2007/094174
PCT Pub. Date: Aug. 23, 2007

(65) Prior Publication Data
US 2009/0177078 A1    Jul. 9, 2009

(30) Foreign Application Priority Data
Feb. 13, 2006  (JP) .................................. 2006-035308

(51) Int. Cl.
*A61B 5/05*    (2006.01)

(52) U.S. Cl.
USPC .......................................................... 600/415

(58) Field of Classification Search
None
See application file for complete search history.

(56) References Cited

U.S. PATENT DOCUMENTS

| | | | | |
|---|---|---|---|---|
| 5,151,656 | A * | 9/1992 | Maier et al. | 324/309 |
| 5,928,146 | A * | 7/1999 | Itagaki et al. | 600/410 |
| 6,897,655 | B2 * | 5/2005 | Brittain et al. | 324/309 |
| 7,110,805 | B2 | 9/2006 | Machida | |
| 2002/0115929 | A1 * | 8/2002 | Machida | 600/410 |
| 2002/0140423 | A1 | 10/2002 | Brittain | |
| 2002/0143247 | A1 | 10/2002 | Brittain et al. | |
| 2003/0011369 | A1 | 1/2003 | Brittain et al. | |
| 2004/0155654 | A1 | 8/2004 | Brittain | |
| 2005/0154291 | A1 * | 7/2005 | Zhao et al. | 600/410 |
| 2006/0184004 | A1 | 8/2006 | Machida | |

FOREIGN PATENT DOCUMENTS

| | | | |
|---|---|---|---|
| JP | 8-173396 | 7/1996 | |
| JP | 2002-95646 | 4/2002 | |
| JP | 2003-135429 | 5/2003 | |
| JP | 2003135429 A * | 5/2003 | ............. A61B 5/055 |

OTHER PUBLICATIONS

Cohen, Echo-planar imaging (EPI) and functional MRI, Oct. 5, 2000, p. 1-17.*
Machida et al, Velocity Independent Phase-Shift Stabilization (VIPS) Technique in FSE Flow Imaging, Proc. Intl. Soc. Magn. Reson. Med. the seventh meeting, 1999, p. 1910.*

* cited by examiner

*Primary Examiner* — Long V. Le
*Assistant Examiner* — Bo J Peng
(74) *Attorney, Agent, or Firm* — Cooper & Dunham LLP

(57) ABSTRACT

In the continuous moving table imaging, high-speed imaging such as the echo planar method is implemented without deteriorating image quality, realizing a high-speed table movement, namely, high-speed imaging.
In the magnetic resonance imaging apparatus, an imaging control means for controlling a magnetic field generation means, a transfer means, and a signal processing means executes an imaging sequence for applying multiple readout gradient magnetic fields to measure multiple nuclear magnetic resonance signals, after one-time application of an exciting RF pulse, while moving the transfer means. On this occasion, a positional deviation of the readout gradient magnetic fields given to the multiple nuclear magnetic resonance signals, caused by the movement of the transfer means, is calculated in advance as correction data, so that the measured nuclear magnetic resonance signals are corrected by the correction data.

16 Claims, 12 Drawing Sheets

MAGNETIC RESONANCE IMAGING APPARATUS AND METHOD

TECHNICAL FIELD

The present invention relates to a magnetic resonance imaging (hereinafter, referred to as "MRI") apparatus, which utilizes a nuclear magnetic resonance phenomenon to obtain a tomographic image of an area to be examined of a subject. In particular, it relates to an MRI apparatus that is capable of acquiring at high speed while moving a table, an image of a field of view which is wider than a field being limited within the apparatus.

BACKGROUND ART

In the MRI apparatus, a space having a highly homogeneous static magnetic field, which allows a preferable imaging, is limited to a relatively narrow area, and conventionally, an FOV (field of view) has also been limited within this area. In recent years, even under such restriction, there is proposed a method (hereinafter, referred to as "moving table imaging") for acquiring an image of an area equal to or larger than the homogeneous static magnetic field space, or a total body image, by continuously moving the table on which the subject is placed, while the imaging is performed (for example, patent document 1). This patent document 1 discloses a method in which an operation is repeated for acquiring signals assuming a frequency encoding direction is identical to the table moving direction, while the table is moved in step wise or in continuous manner, and finally, an image is reconstructed from the signals obtained during all the steps of the table moving. This document further describes that echo planer imaging (EPI) mode is available as a method for collecting data.
Patent document 1: Japanese Published Unexamined Patent Application No. 2003-135429

DISCLOSURE OF THE INVENTION

Problem to be Solved by the Invention

In general, the MRI utilizes a readout gradient magnetic field for measuring an echo signal. Nuclear magnetization of slab, which is excited by applying an RF magnetic field, becomes in phase when the readout gradient magnetic field (rephasing gradient) is applied, which is opposite in polarity and having the same strength as the readout gradient magnetic field (dephasing gradient) that has been applied before collecting the magnetization, and is measured in a form of an echo signal. When the moving direction of the table is assumed as a frequency encoding direction (readout direction) in the continuously moving table imaging, a position of magnetization is deviated between the dephasing gradient and the rephasing gradient, due to the table movement, and therefore, the magnetization is not completely in phase. In other words, there is a problem that a signal being measured may include a phase rotation associated with the positional deviation. As for this problem, if a pulse sequence such as the gradient echo method, which measures one signal per one excitation, is employed, all the signals being measured are placed under the same condition, and therefore, it is possible to ignore an influence that may be exerted upon an image being reconstructed.

However, as in the case of the echo planar method, which acquires multiple signals by using inversion of the readout gradient magnetic field after one-time excitation, for instance, if a high-speed imaging method is applied to the moving table imaging, a condition of the readout gradient magnetic field being applied (history of the readout gradient magnetic field until a signal is collected) varies depending on each of the multiple signals. Such variations of the history of the readout gradient magnetic field for each MR signal may cause a generation of artifact and deterioration of image quality.

An object of the present invention is to suppress an artifact or image deterioration, which is caused by a deviation in a relative position of the readout gradient magnetic field on a subject, due to a table movement, when multiple signals are measured after one-time excitation in the moving table imaging and an image is reconstructed by using these multiple signals.

Means to Solve the Problem

In order to achieve the object described above, a magnetic resonance imaging apparatus according to the present invention includes a calculation means for calculating a positional deviation of a readout gradient magnetic field given to multiple nuclear magnetic resonance signals, and correction means for correcting the positional deviation, the positional deviation being caused by a movement of a transfer means, when an imaging sequence is executed for measuring the multiple nuclear magnetic resonance signals after one-time excitation, while a table is continuously moved.

The calculation means for calculating the positional deviation of the readout gradient magnetic field calculates a positional deviation of the readout gradient magnetic field, for example, based on a moving velocity of the transfer means and intervals for measuring the multiple nuclear magnetic resonance signals, or the calculation means further calculates according to the positional deviation, a difference in the readout gradient magnetic field strength, a frequency difference, or a phase difference. Alternatively, the calculation means calculates the positional deviation of the readout gradient magnetic field based on measured data obtained by a preliminary measurement sequence that is made up of the same imaging sequence as a real imaging measurement and does not include a phase encoding, or the calculation means further calculates, according to the positional deviation, a difference in the readout gradient magnetic field strength, a frequency difference, or a phase difference.

The correction means changes a parameter for executing the imaging sequence and corrects the positional deviation. For example, the correction means corrects the readout gradient magnetic field by adding a static magnetic field offset to the readout gradient magnetic field applied when measuring the nuclear magnetic resonance signals, the offset having strength equal to the difference in the readout gradient magnetic field strength calculated in the calculation means. Alternatively, the correction means corrects a reference frequency for measuring the nuclear magnetic resonance signals, by using the frequency difference calculated by the calculation means.

The correction means further corrects the positional deviation as to each of the multiple nuclear magnetic resonance signals. For example, the correction means corrects each nuclear magnetic resonance signal being measured, by using the phase difference calculated in the calculation means.

According to the correction means as described above, before reconstructing the image, it is possible to eliminate an influence caused by the deviation in position where the readout gradient magnetic field is applied, and thereby prevent generation of artifact and deterioration of image quality.

The magnetic resonance imaging apparatus according to the present invention executes a 3D imaging sequence for measuring multiple nuclear magnetic resonance signals by providing the phase encoding of the first axis and the phase encoding of the second axis after one-time excitation, while continuously moving the table, and controls the sequences of phase encoding of a first axis and a second axis in such a manner that all the phase encoding signals of either one of the phase encoding of the first axis and the phase encoding of the second axis are measured at one-time excitation.

The imaging sequence executed by the imaging control means may be, for example, an imaging sequence according to echo planar method, an imaging sequence according to fast spin echo method, multi-shot imaging sequence for acquiring data of all phase encoding by more than one excitation, or an imaging sequence according to 3D echo planar method including the first axis and the second axis phase encoding. When the multi-shot imaging sequence is employed, the imaging control means controls so that the ordering of measuring signals is to be serial in the phase encoding direction. When the 3D echo planar method is employed as the imaging sequence, the imaging control means controls the ordering of measurement so that the all phase encoding signals are acquired by one-time excitation for phase encoding direction of either of the first axis and the second axis, which is orthogonal to the moving direction of the transfer means.

Such control of the calculation sequence allows the acquisition of data being continuous in the K-space, and further enables reconstruction of a wide field of view, by connecting data representing a wide area.

Further in the magnetic resonance imaging apparatus according to the present invention, the imaging control means executes a correction data acquisition sequence that has a sequence form being the same as the imaging sequence, and does not include application of phase encoding gradient pulse, and the correcting means creates correction data from the nuclear magnetic resonance signals obtained in the correction data acquisition sequence and corrects a variation of the readout gradient magnetic field by using the correction data. In this case, the correction data may be subjected to a function fitting, and thereafter used for the correction.

By using the correction data obtained by executing the correction data acquisition sequence, it is possible to correct a deviation of position for applying the readout gradient magnetic field, simultaneously with correcting N/2 artifact that is generated in the imaging pulse sequence of echo planar method. Using the data after functional fitting allows a precise correction without depending on a table position (i.e., a form of the subject) when the correction data is acquired.

Effect of the Invention

According to the present invention, when multiple signals are measured after one-time excitation in the moving table imaging and an image is reconstructed by using these multiple signals, it is possible to suppress an artifact and image quality deterioration, which are generated by a deviation in relative position of the readout gradient magnetic field on the subject, the deviation being caused by movement of the table.

BEST MODE FOR CARRYING OUT THE INVENTION

Hereinafter, embodiments of the MRI apparatus according to the present invention will be explained. It is to be noted here that corresponding elements having the same function are labeled the same in all figures for explaining the embodiments of the invention, and these elements will not be explained tediously.

Firstly, an overview of the MRI apparatus according to the present invention will be explained with reference to FIG. 1. FIG. 1(a) is a block diagram showing an overall configuration of the MRI apparatus according to the present invention, and FIG. 1(b) is a block diagram showing details describing each element. This MRI apparatus includes, as primary components, a static magnetic field generation system 2, a gradient magnetic field generation system 3, a sequencer 4, a transmitting system 5, a receiving system 6, a signal processing system 7, a table driving system 8, and a central processing unit (CPU) 9. The CPU 9 is provided with an arithmetic function for performing computation necessary for the processing in the signal processing system 7, and a control function such as the sequencer 4 for controlling the entire apparatus.

The static magnetic field generation system 2 generates a homogeneous static magnetic field in the body axis direction or in the direction orthogonal to the body axis direction in the surrounding space of the subject 1, and there are arranged around the subject 1, a magnetic generation means which employs a permanent magnet system, a resistive magnet system, or a superconducting system. The static magnetic field generation system 2 may be provided with a shim coil (not illustrated) for enhancing homogeneities of the static magnetic field.

The gradient magnetic field generation system 3 is made up of gradient magnetic field coils 31 being wound in three directions X, Y, and Z, and a gradient magnetic field power supply 32 for driving each of the gradient magnetic field coils. According to a command from the sequencer 4, the gradient magnetic field supply 32 of each of the coils is driven, thereby applying gradient magnetic fields in the three directions of X, Y, or Z to the subject 1. More specifically, by applying one of the gradient magnetic fields of the X, Y, and Z directions, or more than one of the gradient magnetic fields of the X, Y, and Z directions being combined, a slice gradient pulse (Gs) is applied, and thereby setting a slice plane for the subject 1. Simultaneously, two directions orthogonal to the slice direction, a phase encoding gradient pulse (Gp) and a frequency encoding gradient pulse (Gf) are applied, and thereby encoding an echo signal with positional information of each of the directions.

In the present invention, these axes of the gradient pulses can be arbitrary determined with respect to the apparatus coordinate system (X, Y, and Z). However, the present invention can be preferably applied when the frequency encoding direction is the same as the table moving direction.

The sequencer 4 is an imaging control means for repeatedly applying an RF magnetic field pulse (hereinafter, referred to as "RF pulse") and the gradient pulses at a predetermined pulse sequence, and the sequencer is activated by a control from the CPU 9 to transmit various commands required for collecting tomographic image data of the subject 1, to the transmitting system 5, the gradient magnetic field generation system 3, the receiving system 6, and the table driving system 8. Operations of the sequencer 4 will be described in detail below.

The transmitting system 5 irradiates an RF pulse, so as to excite a nuclear magnetic resonance in a nuclear spin of each atomic element constituting a living tissue of the subject 1, and the transmitting system is made up of an RF oscillator 51, a modulator 52, an RF amplifier 53, and an RF coil 54 on the sending side. An RF pulse outputted from the RF oscillator 51 is subjected to an amplitude modulation by the modulator 52 at the timing according to a command from the sequencer 4, and the RF pulse being subjected to the amplitude modulation is amplified by the RF amplifier 53. Thereafter, the pulse is supplied to the RF coil 54 placed in proximity to the subject 1, whereby an electromagnetic wave (RF pulse) is irradiated on the subject 1.

The receiving system 6 detects an echo signal (NMR signal) emitted by the nuclear magnetic resonance in the nuclear spin constituting the living tissue of the subject 1, and the receiving system is made up of an RF coil 61 on the receiving side, an amplifier 62, a quadrature phase detector 63, and an A/D converter 64. A response electromagnetic wave (NMR signal) from the subject 1, which is induced by an electromagnetic wave irradiated from the RF coil 54 on the sending side is detected by the RF coil 61 arranged in proximity to the subject 1, and the NMR signal is amplified by the amplifier 62. Thereafter, the signal is divided into orthogonal two-system signals by the quadrature phase detector 63 at the timing indicated by a command from the sequencer 4, and then, each divided signal is converted into a digital quantity by the A/D converter 64, and transferred to the signal processing system 7.

The signal processing system 7 includes an external storage unit such as a part of the CPU 9, an optical disk 71, and a magnetic disk 72, a display 73 made up of CRT and the like, and an operation unit 74. When data from the receiving system 6 is inputted into the CPU 9, the CPU 9 executes a processing such as a signal processing and an image reconstruction, and displays a resulting tomographic image of the subject 1 on the display 73, as well as recording the image in the external storage unit such as the magnetic disk 72. The operation unit 74 is prepared for inputting various control information of the MRI apparatus and control information of the processing performed in the signal processing system 7, and the operation unit is made up of a track ball or a mouse 741, a keyboard 742, and the like.

The table driving system 8 includes a table 81 for placing the subject 1 thereon, a table moving mechanism 82 for moving the table 81 in the vertical direction and the horizontal direction, and a table controller 83 for controlling the table movement in association with a pulse sequence according to the control from the sequencer 4 or the CPU 9. In addition, the table moving mechanism 82 is provided with a position detecting unit (not illustrated) for detecting the position of the table 81. The table controller 83 controls the table movement by using the positional information from the position detecting unit, and provides the signal processing system with the information such as correction amount necessary for an MR signal.

In the present embodiment, there will be explained a case that the table 81 is moved to a highly homogeneous static magnetic field space (imaging space) 21, which is generated by the static magnetic field generation system 2, and a wide range of the subject 1 (a range wider than the aforementioned imaging space) is taken as an image. However, the relationship between the static magnetic field generation system 2 and the table 81 is relatively determined, and it is further possible that the static magnetic field generation system 2 is provided with a moving mechanism allowing the system itself to move, with respect to the table being static.

The sequencer 4 follows the pulse sequence being set in advance to control the gradient magnetic field generation system 3, transmitting system 5, receiving system 6, signal processing system 7, and table driving system 8, and repeats excitation of a specific area of the subject 1 positioned in the imaging space and collection of signals from the specific area, while continuously moving the table. As for the pulse sequence, various sequences depending on the imaging method are stored in the storage unit of the CPU 9, and it is configured such that a desired pulse sequence is selected via the operation unit 74, simultaneously setting parameters necessary for the imaging. The pulse sequence executed in the present invention is a multi-echo sequence for measuring multiple signals after one-time excitation by applying an RF pulse. This pulse sequence incorporates correction of signals in response to an interval (echo interval) for measuring the multiple signals and the moving amount of the table which moves during the interval.

Next, an operation of the MRI apparatus having the configuration above will be explained. For easy understanding the present invention, with reference to FIG. 10 and FIG. 11, an overview of a conventional continuous moving table imaging will be explained. FIG. 10(*a*) illustrates an example of the pulse sequence that is employed in the conventional continuous moving table imaging. This pulse sequence indicates a pulse sequence according to a publicly known gradient echo method, and one echo signal 206 is acquired for each RF pulse irradiation 201. Repetition of the operation from the RF pulse irradiation 201 to one echo signal acquisition, every repetition time interval TR (208), allows acquisition of all echo signals necessary for reconstructing an image. In the figure, the terms "Gs", "Gp", "Gr" are lines representing application of the slice gradient magnetic field, the phase encoding gradient magnetic field, the readout gradient magnetic field (frequency encoding gradient magnetic field), respectively, and the reference numeral 202 represents a slice gradient pulse, 203 represents a phase encoding gradient pulse, 204 represents a readout gradient pulse, and 205 represents a sampling window that performs AD conversion. In general MRI, these gradient magnetic fields can be set on any axis. However, in the continuous moving table imaging as shown in FIG. 11, the readout gradient is set in the table moving direction (x-direction), and two directions orthogonal thereto are set as the slice direction and phase encoding direction, respectively. Any direction orthogonal to the x-direction can be set as the slice direction and the phase encoding direction. However, in FIG. 11(*a*) and FIG. 11(*b*), it is shown the case where the z-direction indicates the slice direction, in other words, the case where an imaging section is set horizontally with respect to the table 81. In another embodiment of the present invention described below, it will be explained that the slice direction and the phase encoding direction are set to be the same as the case of FIG. 11, but this example does not restrict the scope of the invention.

The pulse sequence as shown in FIG. 10(*a*) is repeated until the all the echo signals 206 for the entire phase encoding are acquired, and data elements 206-1 to 206-11 that fill the k-space (Ky-Kx space) as shown in FIG. 10(*b*) are measured collectively. Here, if the imaging is performed while the table 81 is moved, the imaging position of the subject 1 with respect to the center of the static magnetic field is moved in the direction (direction indicated by arrow B in FIG. 11) opposite to the table moving direction (direction indicated by arrow A in FIG. 11), from the position 301 when the imaging is started. Accordingly, the readout gradient is applied to a part which is deviated from a part of the subject 1 in halting state. As a result, after the signals of all phase encoding are subjected to Fourier transform in the readout direction, the data obtained is deviated in the direction opposite to the table moving direction as shown in FIG. 11(*c*).

Here, if the table moving velocity V is set to satisfy the following: $V \leq FOVx/(TR \times N)$ (here, FOVx represents FOV size in the readout direction, and N represents phase encoding number), as shown in FIG.

11(d), hybrid data (Ky-x spatial data) being continuous in the readout direction can be obtained. This hybrid data is subjected to Fourier transform in the phase encoding direction, and thereby an image having an FOV wider in the readout direction than the original FOV can be generated.

As described above, the conventional continuous moving table imaging has an advantage that imaging of wider FOV can be performed at a relatively high speed, by setting the table moving direction as the readout direction. However, in order to obtain data being continuous in the readout direction, the table moving velocity is limited by the repetition time TR and the repetition number of times N of the pulse sequence. On the other hand, as a high speed pulse sequence, there is known a pulse sequence such as EPI, which collects multiple signals by one-time excitation (one shot) of RF pulse. By applying this kind of high-speed pulse sequence such as EPI to the continuous moving table imaging, improvement of the table moving velocity and speedup of the imaging can be achieved. However, if the pulse sequence such as EPI is simply combined, the image quality may be deteriorated. This is because the table moves even between the echoes when multiple echo signals are measured after one-time RF irradiation, resulting in that an echo signal may be measured under the condition that a nuclear magnetization, which should be rephased by the readout gradient, has not been rephased yet. Therefore, the present invention applies a single-shot multi-echo imaging method such as EPI to the continuous moving table imaging, while providing a means for substantially eliminating an influence that may be exerted when the readout gradient is applied to a deviated position.

First Embodiment

Hereinafter, as a first embodiment of the present invention, an operation of the MRI apparatus will be explained taking an example that the multi-shot EPI (echo planar imaging) is employed as the pulse sequence. FIG. 2 illustrates a procedure of the operation. In the present embodiment, the operation incorporates, step 101 for calculating a phase correction value, step 102 for obtaining main measurement data, step 103 for correcting a phase of the main measurement data, step 104 for subjecting the corrected main measurement data to Fourier transform in the readout direction, step 105 for connecting the data in the readout direction, and steps 106 and 107 for producing an image, after data collection up to the final position in the table moving range being set in advance.

FIG. 12 illustrates a configuration of the signal processing system (CPU 9) for implementing the operation above. As illustrated, the CPU 9 incorporates, an imaging controller 90, an image arithmetic unit 91 for reconstructing an image by subjecting echo signals measured in the receiving system 6 to Fourier transform and correcting calculation, a phase calculation unit 92 for calculating a phase correction value of each echo, a correction value memory 93 for storing the phase correction value calculated by the phase calculation unit 92, and a main controller 94.

The imaging controller 90 controls imaging operation via the sequencer 4. In the step 101 for calculating the correction phase, the phase calculation unit 92 uses information such as parameters of the pulse sequence set in the sequencer 4 and the table moving velocity set in the table controller 83, so as to calculate a phase deviation (phase correction value), which occurs in each echo due to the table movement when the EPI measurement is performed. The image arithmetic unit 91 reconstructs an image by using the echoes obtained by the moving table imaging (step 104 and step 105). On this occasion, the step 103 for phase correction is executed, and each echo is corrected by using the phase correction value calculated by the phase calculation unit 92. The main controller 94 controls the operations of the imaging controller 90, image arithmetic unit 91, phase calculation unit 92, and correction value memory 93.

The steps, other than the step 101 for calculating a phase correction value and the step 103 for correcting the phase, are approximately the same as the conventional moving table imaging. Firstly, the step 102 for obtaining main measurement data will be explained.

FIG. 3 illustrates an overview of the moving table imaging that is performed in the main measurement, showing a relationship between the subject 1 and the imaging space 301. In the present embodiment, the subject 1 is placed on the table 81 in such a manner that the body axis of the subject 1 is parallel to the moving direction of the table 81 (assumed as x-direction). According to the movement of the table 81, the positional relationship between the imaging space 301 and the subject 1 varies, thereby allowing acquisition of images representing different parts of the subject 1.

FIG. 4 illustrates one example of the pulse sequence employed in the main measurement. This pulse sequence is the same as the publicly known EPI sequence, except that this pulse sequence is executed under the condition that the table is moved at a constant speed. In the figure, "RF", "Gs", "Gp", "Gr", "AD/echo" respectively represent axes of RF pulse, slice gradient, phase encoding gradient, frequency encoding (readout) gradient, and A/D conversion (sampling window)/ echo signal.

In brief, an RF pulse 401 is irradiated on the subject that includes magnetization to be detected, and simultaneously, a slice gradient 402 is applied for selecting a slice (slab), and a slice to be imaged is selected. Next, a phase encoding gradient 403 for providing a phase encoding offset and a readout gradient 405 for giving a readout gradient offset are applied. Then, the phase encoding gradient pulses 404 are applied discretely, readout gradients 406 being inversed, and in respective cycles thereof, a group of echo signals 407 are acquired (in the illustrated example, six echo signals are measured). The sequence as illustrated is repeated for a predetermined number of times ((all phase encoding number)/ (the number of signals collected in one-time excitation)), while varying the magnitude of the phase encoding gradient 403 in a certain repetition time (TR) 408, and the echo signals from all phase encoding are collected. What is significant here that the sequence for acquiring k-space data agrees with the sequence of data array in the phase encoding direction. In other words, it is considered to be desirable to acquire data in sequence from the edge on the k-space without skipping any data. That is, the magnitude of the phase encoding gradient 404 is adjusted to be the magnitude corresponding to one-step of phase encoding, and the variation (offset) of the phase encoding gradient 403 is adjusted to be a value, i.e., (the number of signals collected at one time)×(magnitude corresponding to one-step of phase encoding). This enables to acquire the k-space data which is continuous in the phase encoding direction.

The table moving velocity V during the execution of the pulse sequence is set in such a manner that a distance the table moves during the time T for collecting the all phase encoding data is equal to or shorter than the FOV length FOVx in the readout direction (x-direction). Here, T=TR×N/M: N represents the number of all phase encoding and M represents the number of signals measured by one-shot) In other words, V≤FOVx/T. This relationship is implemented by controlling the table velocity in accordance with the execution time of the pulse sequence (e.g., repetition time). Conversely, this relationship is also implemented by controlling the execution time of the pulse sequence (e.g., repetition time) in accordance with the table moving velocity. Specifically, parameters (repetition time 408, echo interval 412, and the like, in FIG. 4) of the pulse sequence are set in the sequencer 4 via the operation unit 74. When the pulse sequence is determined, the table controller 83 calculates the table moving velocity based on the parameters being set, and controls the table moving mechanism 82 so that the table 81 is allowed to move at the table moving velocity being calculated. Alternatively, when the table moving velocity is set in the table controller 83 via the operation unit 74, the CPU 9 calculates a repetition time of the pulse sequence based on the table moving velocity being set, and sets the calculated repetition time in the sequencer 4.

FIG. 5 illustrates a result after the echo signals being acquired according to the above procedure are arranged in the k-space. FIG. 5(*a*) shows Ky-Kx spatial data, and FIG. 5(*b*) shows data (hybrid data) obtained by subjecting the data in FIG. 5(*a*) to Fourier transform in the readout direction. In the figure, for simplification, there is shown a case where the number of signal being measured at one repetition is four, and the number of repetitions is three. As shown in FIG. 5(*a*), in the present embodiment, the measurement is performed in the direction indicated by arrows, and four echo signals obtained within the one-time repetition (=shot) time 408 are arranged from the lower side of the k-space towards the upper side thereof. Then, since the magnitude of the phase encoding gradient offset 403 given for each shot is different from one another, the start position of the K-space is different shot by shot, and thereby the k-space can be filled by multiple shots 408 (408-1 to 408-3). Here, the readout gradient (frequency encoding gradient) applied in the table moving direction becomes the same as the readout gradient that is applied after shifting in the direction opposite to the table moving direction, and therefore hybrid data 407'-1 to 407'-3 are generated as shown in FIG. 5(*b*). In FIG. 5, elements 408-1, 408-2, and 408-3 correspond to the shot 408 shown in FIG. 4, and the echo trains 407-1, 407-2, and 407-3 correspond to the signal 407 in FIG. 4. It is to be noted here that FIG. 5(*b*) shows an example that the shift amount in the x-direction of each hybrid data is larger than the shift amount in the x-direction for each echo within the same shot. However, it is further possible to make the shift amount in the x-direction of the hybrid data to be the same as the shift amount for each echo within the same shot, by controlling the TR or the excitation position for each shot of the pulse sequence as shown in FIG. 4. In this case, the hybrid space data arrangement may be the same as the arrangement shown in FIG. 11(*c*).

Next, there will be explained the step 103 for correcting the phase of the main measurement data, which has been measured according to the aforementioned procedure, and the step 101 for calculating a phase correction value that is used in the correction step 103.

Firstly, with reference to FIG. 6, an explanation will be made as to an influence that may be exerted when the continuously moving table imaging is applied to the echo planar method. FIG. 6(*a*) shows enlarged illustrations of the readout gradient axis Gr and an echo signal part Echo which are shown in FIG. 4. In the echo planar method, since the polarity of the readout gradient pulse 406 is inversed, even though the table moving direction is kept constant, influence thereof varies depending on the polarity of the readout gradient. In other words, in the period 412-1 as shown in FIG. 6(*a*), it is assumed that a positive readout gradient 406-1-1 is applied. FIG. 6(*b*) shows a positional relationship between the subject 601 and the gradient magnetic field in the case above. In the next period 412-2, a negative readout gradient 406-1-2 is applied. Here, if the table moving direction coincides with the axial direction (x) of the readout gradient, and the table shifts from the left to right in the figure, the subject 601 moves together with the table, and the positional relationship between the subject 601 and the gradient magnetic field indicates a deviation in the x-direction as shown in FIG. 6(*c*) being displaced from the position shown in FIG. 6(*b*). This positional deviation 602 is in proportion to the length of the period 412.

In general, echo signals can be serially acquired in the echo planar method, because the transverse magnetization in the readout gradient direction can be repeatedly rephased by the inversion of the readout gradient. Therefore, it is necessary that the moment of magnetization applied by the gradient pulses 406-1-1 and 406-1-2 becomes zero at each position (x) of the subject. In other words, the gradient pulse 406-1-2 has to be applied to the position indicated by the dotted line in FIG. 6(*c*). However, if the subject is moved while imaging, the position (x) of the subject is changed, resulting in that the gradient pulse 406-1-2 is applied being deviated from the position indicated by the dotted line in FIG. 6(*c*). Therefore, the moment of magnetization after the gradient pulses 406-1-1 and 406-1-2 are applied does not become zero. As a result, there occurs a difference in phase between the echo signals 407-1-1 and 407-1-2 being acquired. Similarly, between the echo signals 407-1-1 and 407-1-3, a difference in phase corresponding to the positional deviation (602+603) may occur in proportion to twice the length of the period 412. If an image is reconstructed leaving such difference in phase, an artifact may occur when Fourier transform is performed in the phase encoding direction.

In the present embodiment, the phase calculation unit 92 obtains a correction value in advance, in association with a difference in phase, which may occur in the echo signals due to the table movement (FIG. 2, step 101). By using this correction value, the difference in phase is removed from the echo signals 407 acquired when the main measurement is performed (step 103). The correction value is calculated as the following. If it is assumed that the table moving velocity is "V" and the echo signal acquisition interval 412 is "IET", the moving amount ΔX, which indicates a distance the table moves during the IET, is expressed by the formula (1):

$$\Delta X = V \times IET \tag{1}$$

On the other hand, the readout gradient output Gr(mT/m) is expressed by the formula (2), using an imaging field of view FOVx in the readout gradient direction, a band BW, and a gyromagnetic ratio γ:

$$Gr = BW/(\gamma \times FOVx) \tag{2}$$

A difference in magnetic field output caused by the positional shift ΔX is expressed by the formula (3)

$$Gr \times \Delta X = BW/(\gamma \times FOVx) \times \Delta X \tag{3}$$

When the value above is converted to a difference in angular frequency Δω, it is expressed by the formula (4):

$$\Delta \omega = \gamma \times Gr \times \Delta X = BW \times \Delta X / FOVx \tag{4}$$

The difference in angular frequency Δω caused by the positional deviation corresponds to a phase θ of the echo signal expressed by the formula (5):

$$\theta = \Delta \omega \times \Delta t \text{ MOD } 2\pi \tag{5}$$

(In the formula (5), "Δt" represents an application time of the readout gradient pulse, and "a MOD b" represents a reminder obtained by diving "a" by "b".

As thus described, if the table moving velocity V, the length IET of the echo signal acquisition interval 412, and conditions of the readout gradient (outputs, application time) are known, it is possible to calculate a phase difference that is caused by the positional deviation, according to the formulas (1) to (5). These numerical values V, IET, and readout gradient conditions are determined when the pulse sequence is fixed. Therefore, in step 101, a correction value is calculated on the basis of the pulse sequence having been set. The calculated correction value is stored in the correction value memory 93 within the CPU 9, for instance.

The image arithmetic unit 91 uses the phase (correction value) obtained in the correction phase calculating step 101, to correct the phase of the main measurement data being obtained (in FIG. 2, main measurement data phase correcting step 103). Subsequently, the main measurement data after the phase correction is subjected to Fourier transform in the readout direction (step 104), and data (x, ky) being obtained is arranged in association with the position x, in the space for an image (hybrid space: horizontal axis represents the position x, and vertical axis represents the phase encoding Ky) (step 105). As shown in FIG. 4, the echo planar sequence includes as to each shot, a time period 411 until the start of echo signal acquisition, and a time period 413 after the echo signal acquisition to the next RF pulse irradiation 401. Since the table continues moving at the velocity V during the periods above, the position of the table that has moved after the lapse of the those time periods (i.e., a total of the period 411 and the period 413) is obtained, so as to arrange data at a proper position.

The aforementioned step 102 for main measurement to the step 105 for connecting data in the readout direction are repeated until acquiring final data, and all the data necessary for reconstructing an image is obtained (step 106). As already described, the table moving velocity V is set to be equal to or less than the value obtained by dividing the FOV length FOVx in the readout direction (x-direction) by the time T for collecting all phase encoding data. Therefore, the hybrid data obtained in step 106 becomes the data being continuous in the table moving direction, similar to the case as shown in FIG. 11(*d*).

From the hybrid spatial data finally bound, data items on both edges in the x-direction, which are incomplete in the phase encoding direction, are removed as appropriate. Thereafter, the data is subjected to Fourier transform in the phase encoding direction, and then creating an image having a range wider than the FOV defined in the apparatus (step 106 and step 107).

According to the present embodiment, the echo planar method is applied to the table moving imaging, and thereby the table moving velocity can be enhanced by 1/M (M represents the number of signals measured by one shot), compared to the conventional method. Furthermore, a phase difference between the echo signals, which occurs in the situation above, is corrected by the correction value calculated in advance, whereby it is possible to obtain a wide FOV image with reduced artifact.

In the present embodiment, a change of position during the acquisition of echo signals (within the sampling window) is not considered. In other words, since the position varies due to the movement of the table during the time when the echo signal are being acquired, there may be a phase deviation, even slightly, between the data items in the time-series data having been sampled. However, in the echo planar method, the echo interval IET is generally set to be a few micrometers, so as to avoid an image distortion. Therefore, even if the table moving velocity is extremely high such as 100 mm/s (=0.1 mm/ms), a distance the table moves during the IET is 1 mm or less. Since a general spatial resolution of the MRI is approximately 0.5 mm, it is considered that the data within the echo is not deteriorated even though the position moves during the imaging.

However, if the positional change during the acquisition of the echo signal should be removed, the formula (3') is employed as an exact solution, which introduces a concept of time variable into the formula (3), and the calculation is performed on the basis of the formulas (3') to (5'):

$$Gr \times \Delta X(t) = BW/(\gamma \times FOVx) \times \Delta X(t) \quad (3')$$

$$\Delta\omega(t) = \gamma \times Gr \times \Delta X(t) = BW \times \Delta X(t)/FOVx \quad (4')$$

$$\theta(t) = \int \Delta\omega(t)dt \text{ MOD} 2\pi \quad (5')$$

In the embodiment described above, there has been explained a case where the first echo signal out of the multiple echo signals collected after one-excitation is set as a reference, and a phase difference is calculated based on the first echo signal, and then, the phase is corrected. More preferably, the first echo itself is also corrected. In other words, an elapsed time from the pulse 405 that gives an offset of the readout gradient to the first readout gradient pulse 406 is obtained, and according to a distance where the table has moved during that time, the phase at the time when the first echo signal is measured is also calculated, and using this phase as a correction value, the first echo is corrected. Accordingly, more precise correction can be performed.

Further in the embodiment described above, there has been explained a case where signals after the measurement are corrected by using the phase obtained in step 101 for correction phase calculation. However, such ex-post correction is not the only example, but it is alternatively possible to change signal receiving conditions or readout gradient conditions, upon measuring echoes in the main measurement, and thereby reducing an error which may occur in each echo due to the table movement. In this case, the step 101 for correction phase calculation in FIG. 2 is changed to a step for calculating frequency difference, or a step for calculating a static magnetic field offset.

Specifically, the phase calculation unit 92 uses the table moving velocity V, echo signal acquisition interval IET, readout gradient output Gr, imaging field of view FOVx in the readout gradient direction, band BW, and gyromagnetic ratio γ, so as to calculate a frequency difference Δω according to the aforementioned formulas (1) to (4) (frequency difference calculation step). Next, when an echo signal is received in step 102 for obtaining main measurement data, the echo signal is received by displacing the reference frequency only by Δω, which is calculated in the aforementioned formula (4). With the procedure above, it is possible to reduce the image quality deterioration which is caused by the table movement.

Alternatively, the phase calculation unit 92 may calculate a magnetic field output difference GrΔX according to the formula (3) described above. Next, when an echo signal is detected in the step 102 for obtaining echo data in main measurement (when the readout gradient 406 is applied), a static magnetic field offset corresponding to the magnetic field output difference obtained in the formula (3) above is applied. The static magnetic field offset as such can be implemented by driving a shim coil, if the static magnetic field generation system is provided with the shim coil. Also in this case, it is possible to reduce the image quality deterioration which is caused by the table movement.

It is to be noted that the aforementioned three correction methods, i.e., the method of ex-post phase correction, the method for receiving the echo signal by displacing the reference frequency upon detecting the signal, and the method for applying the static magnetic field offset, may be employed independently, or two or three thereof may be combined and executed.

In the embodiment above, there has been explained a case where the present invention is applied to the multi-shot EPI. However, it is understood that the present invention can also be employed to a single-shot EPI, in which all phase encoding signals are measured by one-time excitation (single shot). In addition, the embodiment above is explained taking 2D imaging as an example, but 3D imaging is also applicable.

Second Embodiment

Hereinafter, as the second embodiment of the present invention, 3D-EPI is taken as an example to explain the case where 3D imaging is performed. FIG. 7 illustrates a pulse sequence of 3D-EPI. In the pulse sequence of 3D-EPI, encoding pulses are used in each of the slice gradient direction (Kz) and the phase encoding gradient direction (Ky). In the conventional 3D-EPI, it is possible to set the sequence arbitrarily, i.e., the order how the slice encoding pulses and the phase encoding pulses are applied. In general, a slice encoding loop, in which the application amount varies with respect to each TR similar to the element 403, is added to the slice axis (Gs) of the 2D-EPI pulse sequence as shown in FIG. 4.

On the other hand, in the continuous moving table imaging according to the present invention, the application order of the slice encoding pulse and the phase encoding pulse is configured in such a manner that multiple signals different in phase encoding, which are measured in the same slice encoding, have the same readout gradient conditions.

Specifically, in the present embodiment, as shown in FIG. 7(*a*), the gradient pulses 702 are used for the slice selection gradient 701 with respect to each echo train 407, and thereby all the echo signals necessary for the slice (Kz) direction are acquired just by one-shot. FIG. 7(*b*) illustrates Kz-Ky spatial data of the echo signals which are obtained by one-shot. Data string 703 in the slice direction (Kz) is acquired every shot, and the sequence is repeatedly executed, while varying the amount of pulses 403 that gives offset in the phase encoding direction (Ky) in each shot. Consequently, data items 703-1, 703-2, 703-3, and the like, are acquired in the Ky direction. FIG. 7(*c*) illustrates Kz-Ky spatial data of the echo signals obtained by the repetition. The elements 703-1, 703-2, and the like, in FIG. 7(*c*) respectively indicate echo signals, which are obtained in one shot. The multiple points arranged vertically in the Kz direction are each corresponding to one echo signal. It is to be noted here that FIG. 7(*c*) is a plan view, which is viewed from the direction being vertical to the z-Ky plane in FIG. 11.

While executing this pulse sequence, the table moving velocity V is assumed as the following: V≤FOVx/(N×TR) (here, FOVx represents an FOV size in the table moving direction (x-direction), N represents the phase encoding number, and TR represents the repetition time 408).

When the application order of the slice encoding pulse and the phase encoding pulse is controlled as thus described, as to the signals of an identical slice encoding, all phase encoding signals become to be measured under the same readout gradient conditions. In other words, in the first slice encoding, signals of all phase encoding are measured at the first echo train, in the second slice encoding, signals of the all phase encoding are measured at the second echo train 407, and in the third slice encoding, signals of the all phase encoding are measured at the third echo train (the rest continues in the same way). The Ky-x space arrangement, which is obtained by performing Fourier transform on the obtained data in the Kz direction, becomes to be the same as shown in FIG. 11(*c*).

In the 3D imaging as thus described, the data measuring order is controlled, and the table moving velocity V is controlled as well, as expressed by the formula as described above. Consequently, it is possible to obtain data being continuous in the table moving direction. Furthermore, in the same slice encoding, the readout gradient conditions become the same with respect to each echo signal, and a problem of positional deviation will not occur. Therefore, it is possible to obtain a preferable image, even without performing a phase correction.

Here, as for the slice encoding direction, a difference may occur in the gradient magnetic field strength in the signals measured in one-shot by a positional shift due to the table movement. However, in the 3D imaging, the image quality of the moving table imaging can be improved by eliminating the difference in gradient magnetic field strength within the same slice encoding. In addition, the image quality can be further improved by using uniform readout gradient conditions as for the signals in each of the slice encoding. The imaging procedure in this case may be the same as the first embodiment, except the step 102 for obtaining data in main measurement employs the 3D-EPI, and the multiple echo signals obtained in one-shot are corrected in the same manner as described in the first embodiment.

Specifically, by using a distance ΔX by which the table (subject) has moved during the echo signal acquisition interval 412, a phase difference is obtained in advance according to the formulas (3) to (5) or the formulas (3') to (5'). Then, the acquired signals are corrected. Also in this case, similar to the first embodiment, it is further possible that an elapsed time from the pulse 405 that gives the readout gradient offset until the first readout gradient pulse 406 is obtained, and according to the moved distance of the table during the elapsed time, a phase at the time of measuring the first echo signal is calculated, and then, using this calculated phase as a correction value, the first echo is corrected.

Instead of correcting the signals after the acquisition by using the phase correction value, a reference frequency upon receiving a signal may be made to shift or a static magnetic field offset is given in response to the phase difference, and thereby correcting an effect of the readout gradient 406 that is given to the echo signal as being deviated due to the movement of the subject during the echo signal acquisition interval 412. Thereafter, the acquired data is subjected to Fourier transform in the readout direction, all the data items up to the final data are bound, and then, subjected to Fourier transform in the slice direction and in the phase encoding direction, so as to produce 3D-image data.

According to the present embodiment, even in the continuous moving table imaging, data continuity is not lost, and three-dimensional data can be obtained at a high speed. It is to be noted here that in the three-dimensional imaging, any directions can be assumed as the slice gradient direction, the phase encoding gradient direction, and the readout gradient direction. However, in the present embodiment, it is preferable to select an axis having less data acquiring points as the slice direction, out of the two axes being orthogonal to the table moving direction (=the readout gradient direction).

Third Embodiment

Next, an embodiment will be explained, which uses a pulse sequence according to FSE (Fast Spin Echo) method. The imaging procedure of the present embodiment is the same as the first embodiment, except that the main data measuring step 102 in the flow as shown in FIG. 2 is the FSE sequence.

In the FSE sequence as shown in FIG. 8(a), after magnetization is excited by the RF pulse 801, while the inversion RF pulses 803-1 to 803-3 are successively applied every time intervals 802, the readout pulses 804-1 to 804-3 and the phase encoding gradient pulses 805-1 to 805-6 are applied at predetermined intervals, and thereby the echo signal 806-1 to 806-3 are successively generated.

Also in this pulse sequence, an integral quantity of the strength of the gradient magnetic pulses given to the readout gradient direction (X) at a point of time for measuring each echo signal varies depending on the signals. FIG. 8(b) and FIG. 8(c) each illustrates the integral quantity of the gradient magnetic pulse strength given to the readout gradient direction (X), respectively in the case where the table does not move during the imaging, and in the case where the table moves during the imaging. In the figure, the reference numeral 808 (808-1 to 808-3) represents an application timing of the inversion RF pulse 803, the reference numeral 809 (809-1 to 809-3) represents a point of time when the echo signal shows a peak. If the table does not move during the imaging, as shown in FIG. 8(b), at the time 809 of the peak position of the echo signal, the integral quantity of the gradient magnetic field in the readout gradient direction (X) is equal to zero. On the other hand, if the table is moving, as shown in FIG. 8(c), the position for applying the gradient magnetic field varies according to the change of the table position, therefore, the integral quantity of the gradient magnetic field does not become zero at the time 809 of the original peak position of the echo signal. Therefore, the peak position of the echo signal makes a shift. This indicates that a gradient magnetic field having strength larger or smaller than the readout gradient is given, which is to make the integral quantity to zero at the time 809 as shown in FIG. 8(b).

A difference in the gradient strength (a difference between the gradient strength to be given for making the integral quantity to zero, and the gradient strength actually applied) can be calculated from the aforementioned formula (3) by using positional deviation ΔX obtained from the echo signal acquisition interval and the table moving velocity, if the initially measured echo 806-1 is set as a reference. If the elapsed time is used, from the pulse 804-0 that gives the readout gradient offset until the echo 806-1 that is initially measured, it is also possible to calculate a difference in the gradient magnetic field strength as to the first echo 806-1 as well, according to the table moved distance during the elapsed time. On the basis of the difference in gradient magnetic field strength having been calculated, a phase difference is calculated, using the aforementioned formulas (3) to (5) or (3') to (5'), and echo signals measured are corrected as to each signal, by using the calculated phase difference. The operation, in which the signal having been corrected are subjected to Fourier transform in the readout direction and data connecting and thereafter further subjected to Fourier transform in the phase encoding direction so that an image is created, is the same as the first embodiment and the second embodiment.

Also in the present embodiment, instead of correcting the measured signals, it is possible to correct a frequency reference upon receiving a signal by using the angular frequency difference according to the formula (4), or to give the static magnetic field offset according to the formula (3), and thereby signals, in which a peak deviation due to the gradient strength difference is resolved, may be collected.

According to the present embodiment, the FSE sequence is applied to the continuous moving table imaging, and it is possible to obtain a wide area image at a high speed and without any artifact.

Fourth Embodiment

Next, a fourth embodiment will be explained, which has a different method for acquiring a correction value. In the embodiment described above, it has been explained a case where a correction value is calculated in advance based on the imaging conditions (parameters of the pulse sequence and table moving velocity). In the present embodiment, the correction value is acquired by a preliminary measurement, and the acquired correction value is used for correcting the measured signal, correcting the frequency when a signal is received, or correcting the static magnetic field offset.

Also in the present embodiment, the configuration of the signal processing system is the same as the configuration shown in FIG. 12. However, following points are different; the sequencer 4 executes a sequence of the preliminary measurement, and the phase calculation unit 92 calculates the correction value, by using a signal obtained by the preliminary measurement, not using the parameters set in the sequencer 4. Hereinafter, a method for obtaining a correction value by the preliminary measurement will be explained.

FIG. 9(a) illustrates the procedure. The present embodiment is different from the procedure as shown in FIG. 2, in the point that there are step 108 for measuring correction data and step 109 for calculating correction phase. In the step 108 for measuring the correction data, similar to the main measurement, while the table is moved continuously, the correction data acquiring sequence is executed to acquire the correction data. There is employed as the sequence for acquiring correction data, a sequence which has a sequence form being the same as the main measurement sequence, and which does not output only the pulses of the phase encoding gradient axis (in the case of 3D sequence, pulses of the phase encoding gradient axis and of the slice encoding gradient axis) If the main measurement sequence is the pulse sequence as shown in FIG. 4, an echo signal is measured without using the phase encoding gradient magnetic field 403. In this case, a group of data (in the example of FIG. 4, six signals) is acquired while the table is continuously moved, and this group of data may be used as the correction data. Alternatively, correction data is measured more than once at predetermined intervals while moving the table continuously, and the correction data items at multiple table positions may be acquired.

In the step 109 for calculating the correction phase, a phase rotation is calculated as the correction value based on the echo signals measured in the correction data acquisition sequence, the phase rotation corresponding to the positional deviation of the readout gradient due to the table movement. If the correction data items are acquired at predetermined intervals, the correction data that is acquired at the position closest to the position where the main measurement data is measured is selected and used. This makes the correction more precise. However, only one group of data (e.g., data at imaging position of head part) is acquired and if a phase calculated from that data is used for correcting the main measurement data which is acquired at a different table position (e.g., imaging position of abdominal part), the correction cannot be performed properly. In this case, the calculated phase is subjected to fitting by a function, and thereafter, it is set as the correction value. By doing so, even though there is only one group of data, it is possible to perform phase correction without any influence of the region where the subject exists.

The following operations are the same as the first embodiment; by using the correction value calculated in the correction phase calculating step 109, the phase correction of the main measurement data is performed in step 103 after the main measurement, or the references frequency or the static magnetic offset is changed according to the phase correction quantity, when the main measurement data is received.

In the present embodiment, if the pulse sequence of the main measurement and the pulse sequence of the correction data measurement are the sequence according to the echo planar method which acquires multiple echo signals in time series while inverting the readout gradient magnetic field, it is possible to correct N/2 artifact, together with the correction of the positional deviation of the readout gradient magnetic field due to the table movement, which is the object of the present invention.

The N/2 artifact generates when there occurs an error between the calculated value of the pulse sequence and the real output, due to factors such as incompleteness and output response of the gradient pulse, and thereby the center of the sampling and a position where an echo signal is generated are deviated. In the K-space, if the peak position of the echo signal is deviated from the center, there occurs an inverse relationship between the change in phase of an even number echo and that of an odd number echo in the readout direction after Fourier transform, and therefore, an artifact occurs in the image when Fourier transform is performed in the phase encoding direction. This artifact is N/2 artifact. In the present embodiment, the correction data obtained by the correction data acquisition sequence having the same form as the main measurement sequence includes a phase error component that may cause the N/2 artifact. Therefore, by using this correction data, it is possible to correct the N/2 artifact simultaneously with the correction of the positional deviation of the readout gradient magnetic field, the deviation being caused by the table movement.

As discussed above, according to the present embodiment, a signal is acquired while continuously moving the table, aside from the main measurement, and a phase value of the signal is calculated and used as correction data, thereby performing a precise correction. In addition, simultaneously with correcting the positional deviation of the readout gradient magnetic field due to the table movement, N/2 artifact can be corrected. In particular, when the correction data items are obtained at predetermined intervals, the correction data acquired at a position being the closest to the position where the main measurement data is obtained, is selected and used, and thereby more precise correction is possible in accordance with a form and a position of the subject. Even when a group of the correction data is acquired, if a function fitting is performed, it is possible to perform the correction without affected by a difference in the table position (a difference in the form of the subject).

Fifth Embodiment

Next, an example will be explained as a fifth embodiment, in which only N/2 artifact correction data is acquired by the preliminary measurement.

In the fourth embodiment, the correction data is measured while the table is continuously moved. Therefore, the correction data for correcting the positional deviation (phase rotation) of the readout gradient magnetic field caused by the table movement consequently includes N/2 artifact correction data. However, it is possible to acquire the N/2 artifact correction data separately. In the present embodiment, only the N/2 artifact correction data is acquired by the preliminary measurement. FIG. 9(b) illustrates an operational procedure thereof. The details of the steps 118 and 119 in this procedure are different from those of the steps 108 and 109 of the fourth embodiment (flow in FIG. 9(a)). The other steps are the same as those in the fourth embodiment.

In the present embodiment, in the correction data measuring step 118, a pulse sequence according to the echo planar method is executed to obtain the N/2 artifact correction data, in the state where the table is brought to a halt, and N/2 artifact correction data is acquired. This pulse sequence has a form being the same as the pulse sequence of the main measurement, and only the pulses of the phase encoding gradient axis are not outputted from this sequence. The pulse sequence of the main measurement may be any of the single shot EPI, multi-shot EPI, and 3D-EPI.

In the correction phase calculating step 119, similar to the step 101 of the first or the second embodiment, correction data is calculated for correcting the positional deviation (phase rotation) of the readout gradient magnetic field, caused by the table movement, by using the aforementioned formulas (3) to (5), or the formulas (3') to (5'). Subsequently, the main measurement is performed, and the main measurement data is corrected by using the correction data calculated in the correction phase calculating step 119 and the N/2 artifact correction data obtained in the correction data measuring step 118.

Also in the present embodiment, it is preferable to use the N/2 artifact correction data that has been subjected to a functional fitting. In general, main causes of the N/2 artifact are incompleteness and output response of the gradient pulse, and it is considered to be independent of the positional factor of the table (position of the subject). However, by using the data having been subjected to the functional fitting, it is possible to prevent deterioration of correction accuracy, which is caused by a difference between the table position where the N/2 artifact correction data is acquired and the table position where the main measurement data is acquired.

As explained so far, according to each embodiment of the present invention, a high speed imaging such as the echo planar method can be implemented in the continuous moving table imaging, without deteriorating the image quality, and thereby achieving speed-up of table moving, i.e., speed-up of the imaging.

It is to be noted that the present invention is not limited to the embodiments above, and it should be understood that disclosed embodiments are susceptible of modifications without departing from the scope of the invention. It is also noted that the present can be applied to a sequence such as GRASE (Gradient echo And Spin Echo), which combines a gradient echo and a fast spin echo.

DENOTATION OF REFERENCE NUMERALS

Figure 1:
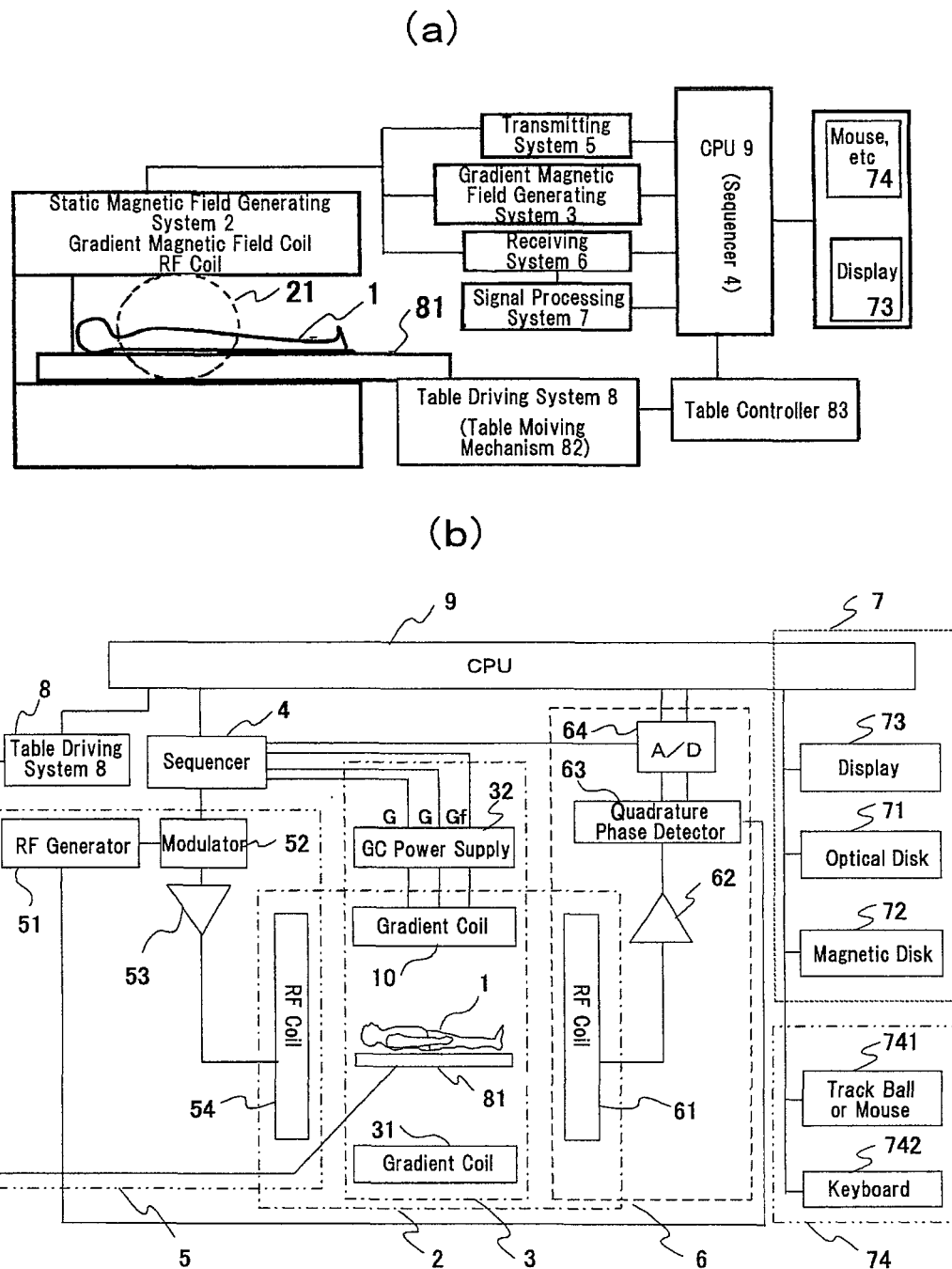
FIG. 1 illustrates an overall configuration of a magnetic resonance imaging apparatus to which the present invention is applied.
Figure 2:
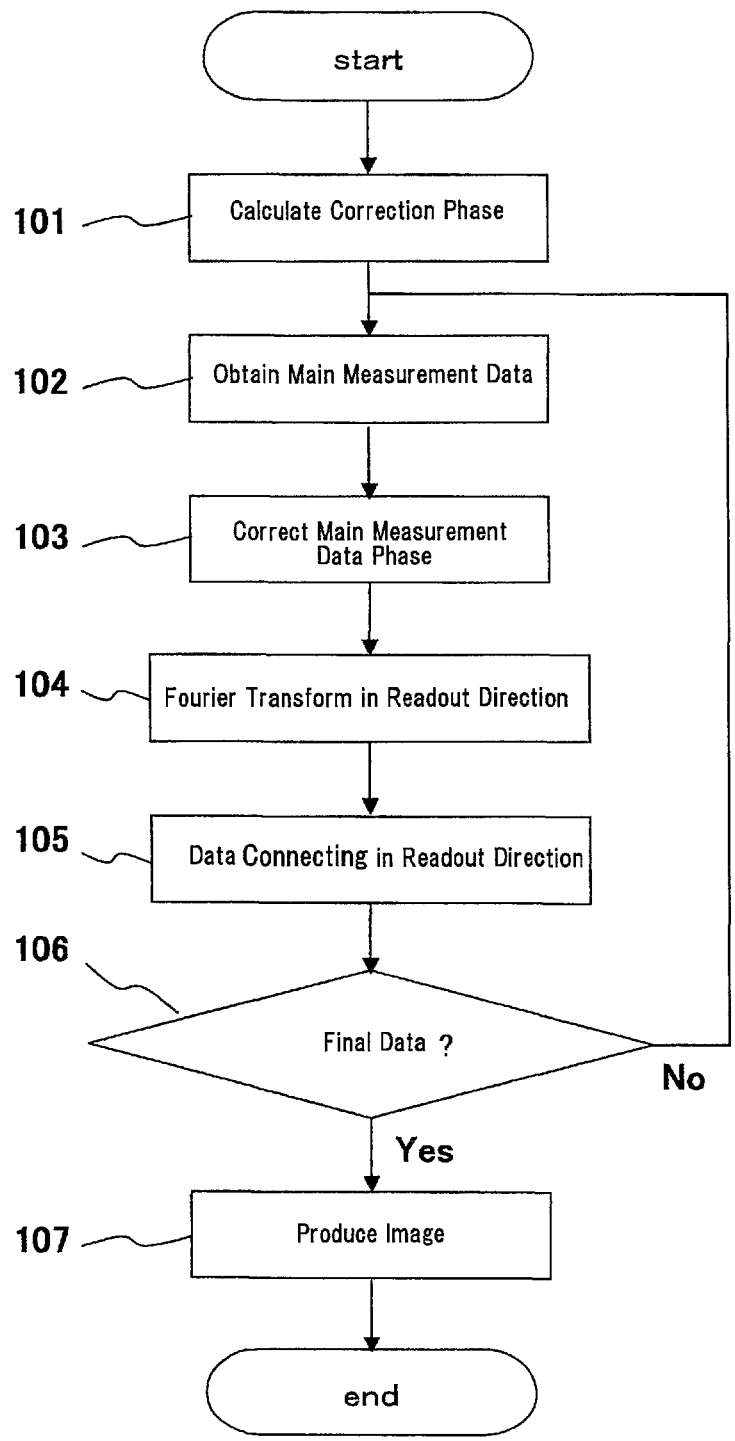
FIG. 2 is a flow indicating the first embodiment of the present invention.
Figure 3:
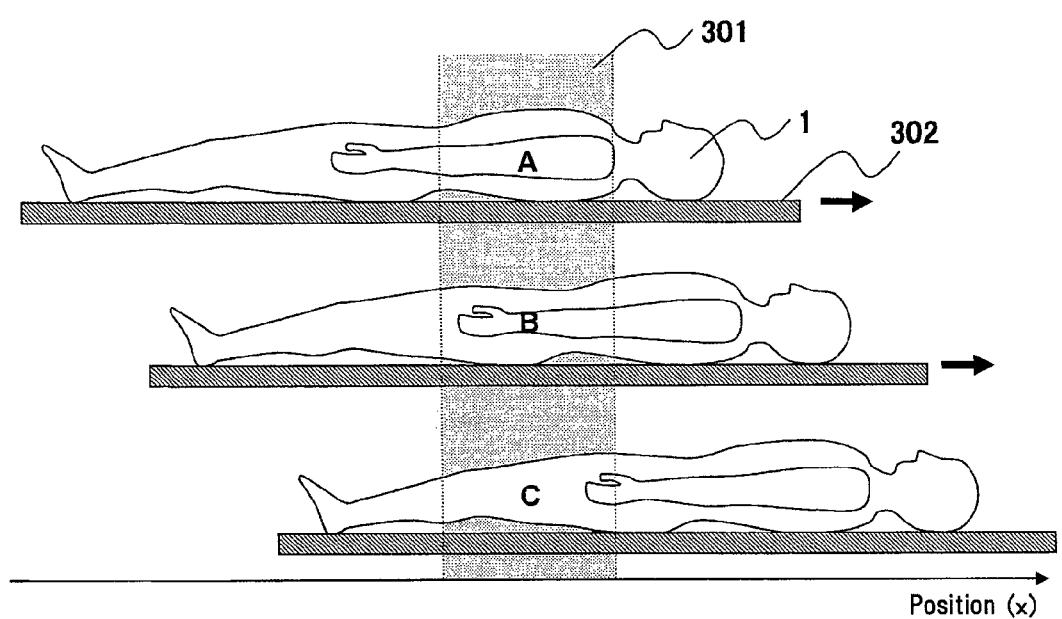
FIG. 3 illustrates a moving table imaging according to the present invention.
Figure 4:
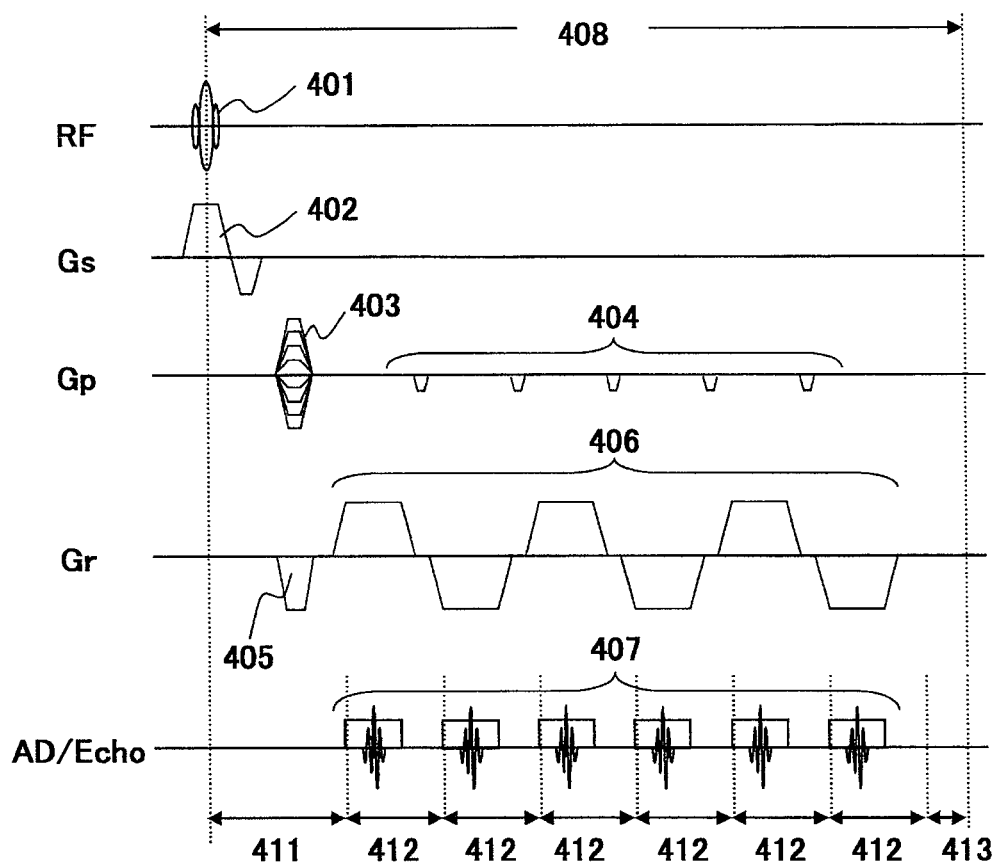
FIG. 4 illustrates a pulse sequence employed in the first embodiment.
Figure 5:
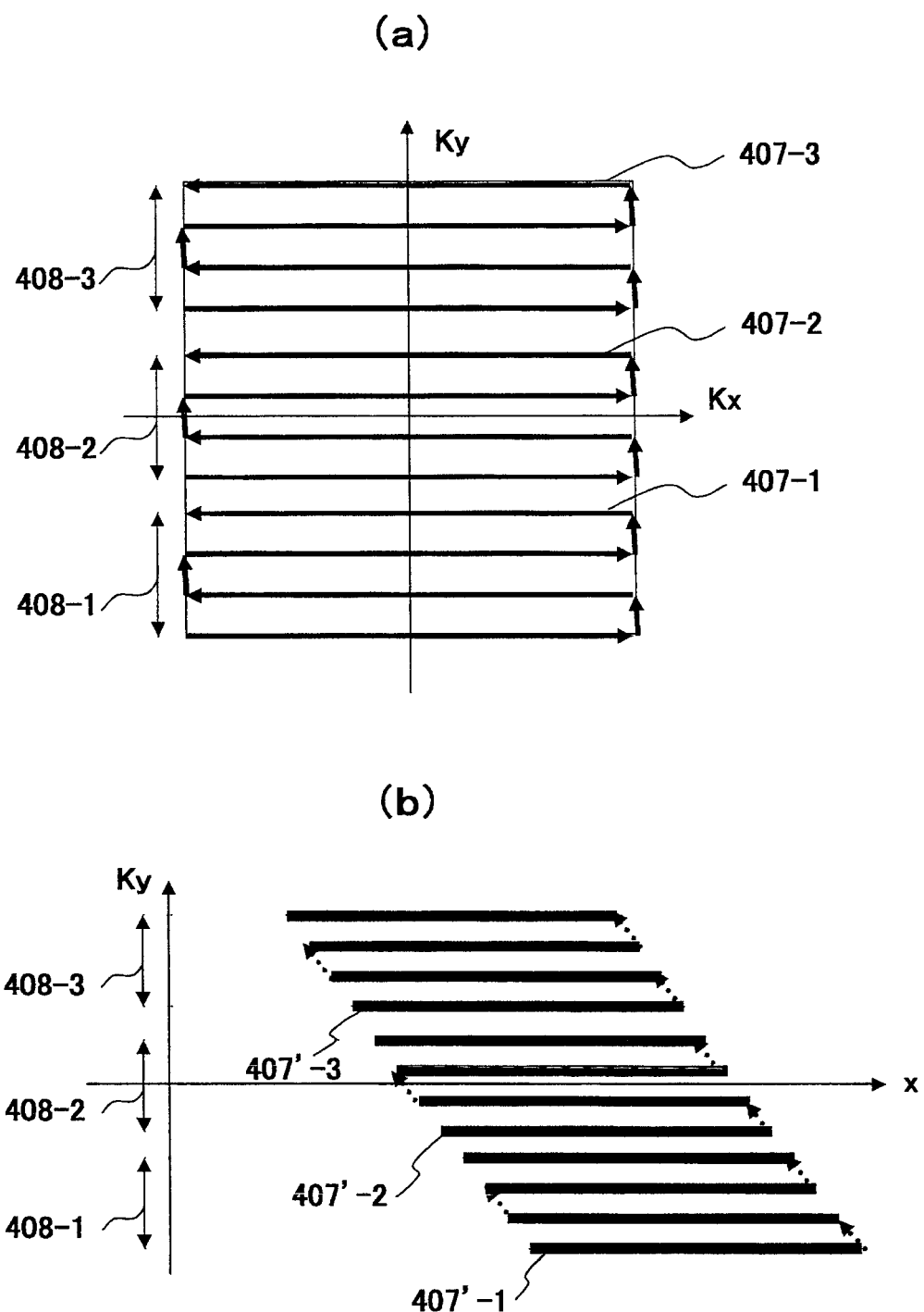
FIG. 5 illustrates K-spatial arrangement of data acquired by the pulse sequence shown in FIG. 4.
Figure 6:
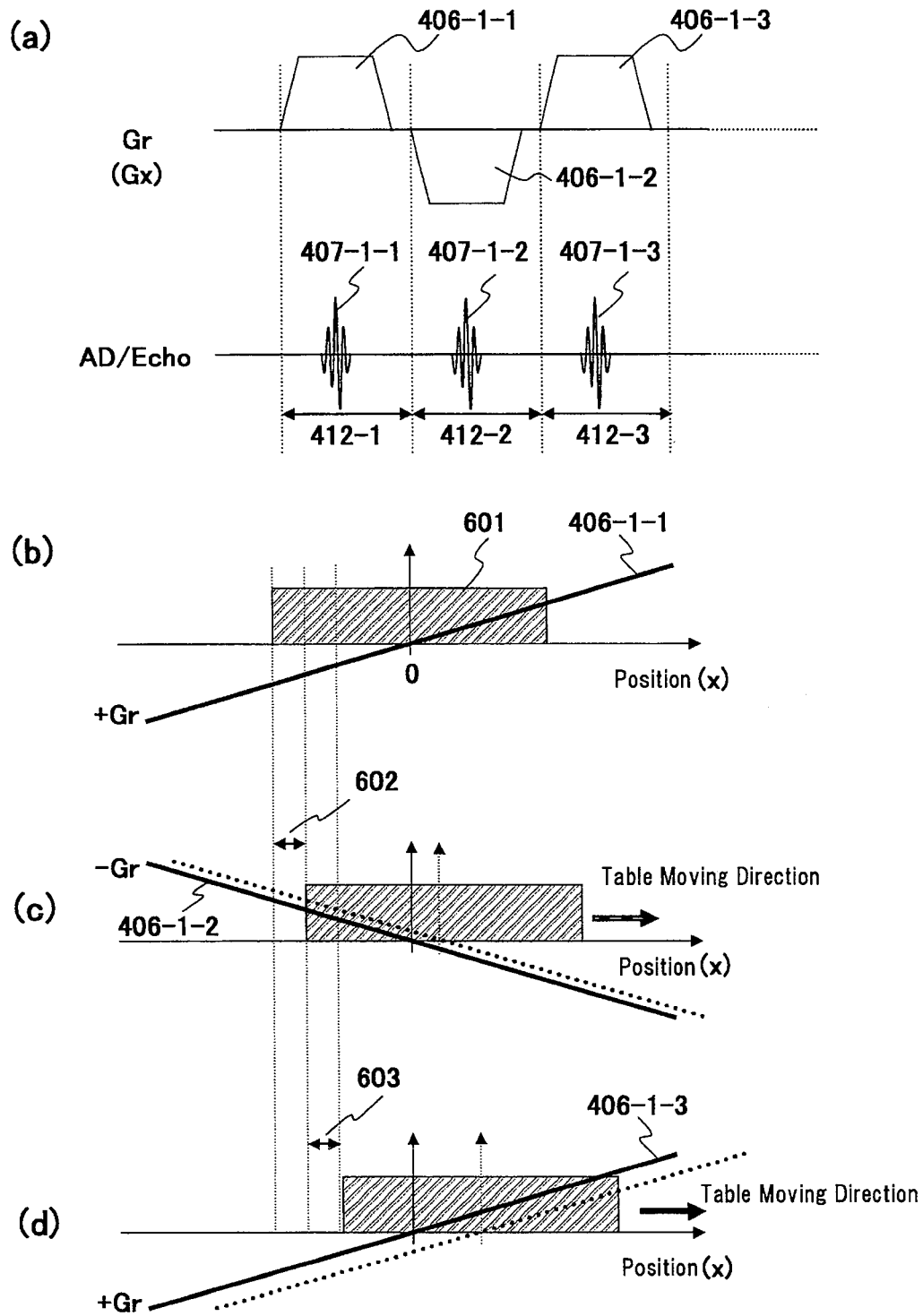
FIG. 6(a) illustrates a part of the pulse sequence shown in FIG. 4, FIG. 6(b) to FIG. 6(d) illustrate positional deviations in the readout gradient magnetic field.
Figure 7:
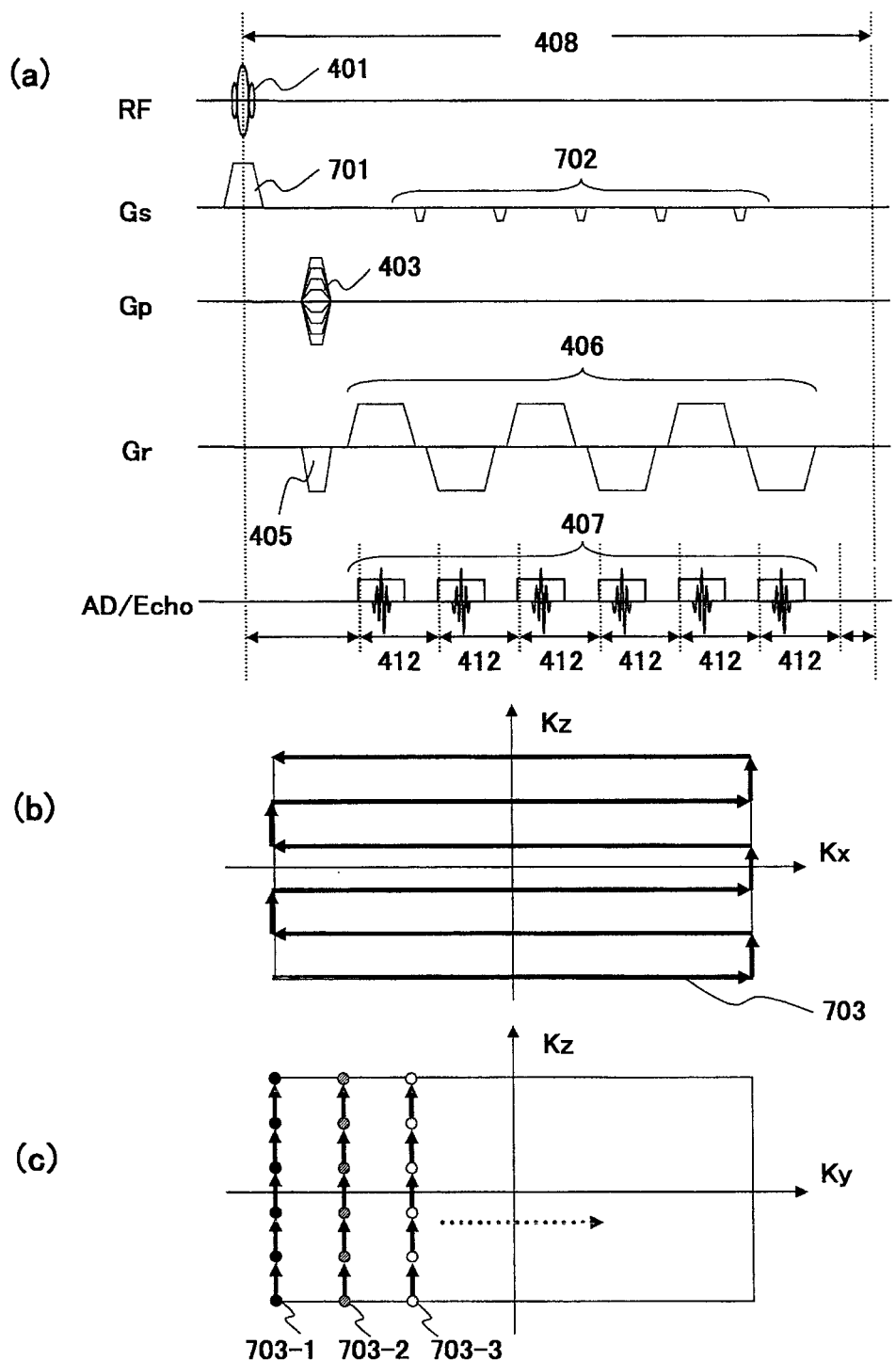
FIG. 7(a) illustrates a pulse sequence that is employed in the second embodiment, FIG. 7(b)
FIG. 7(c) illustrates the measuring order.
Figure 8:
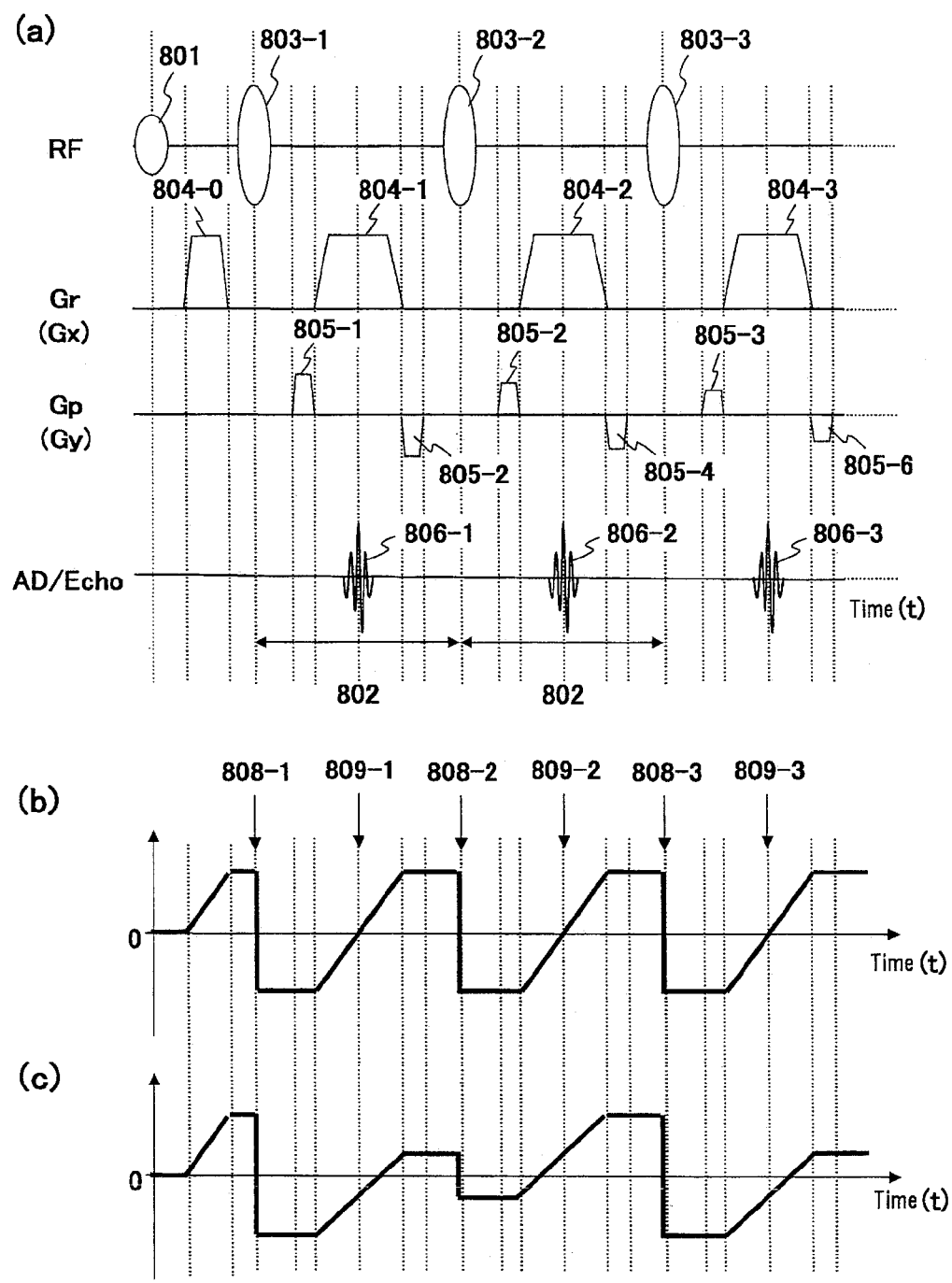
FIG. 8(a) illustrates a pulse sequence that is employed in the third embodiment.
FIG. 8(b) and FIG. 8(c) illustrate an integral quantity of the readout gradient magnetic field, respectively when imaging is performed during the table suspension, and when imaging is performed during the table movement.
Figure 9:
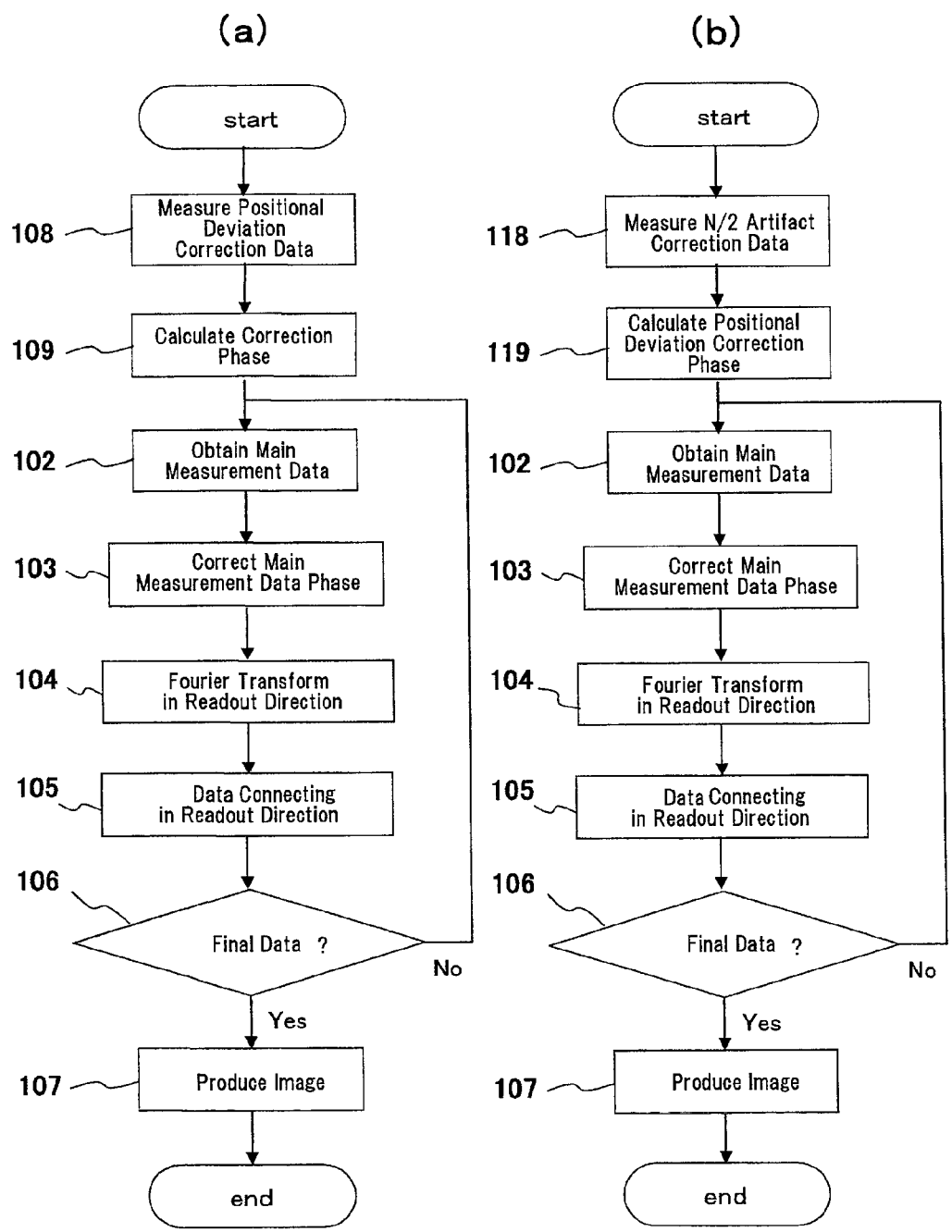
FIG. 9(a) is a flow indicating the operation of the fourth embodiment of the present invention.
FIG. 9(b) is a flow indicating the operation of the fifth embodiment of the present invention.
Figure 10:
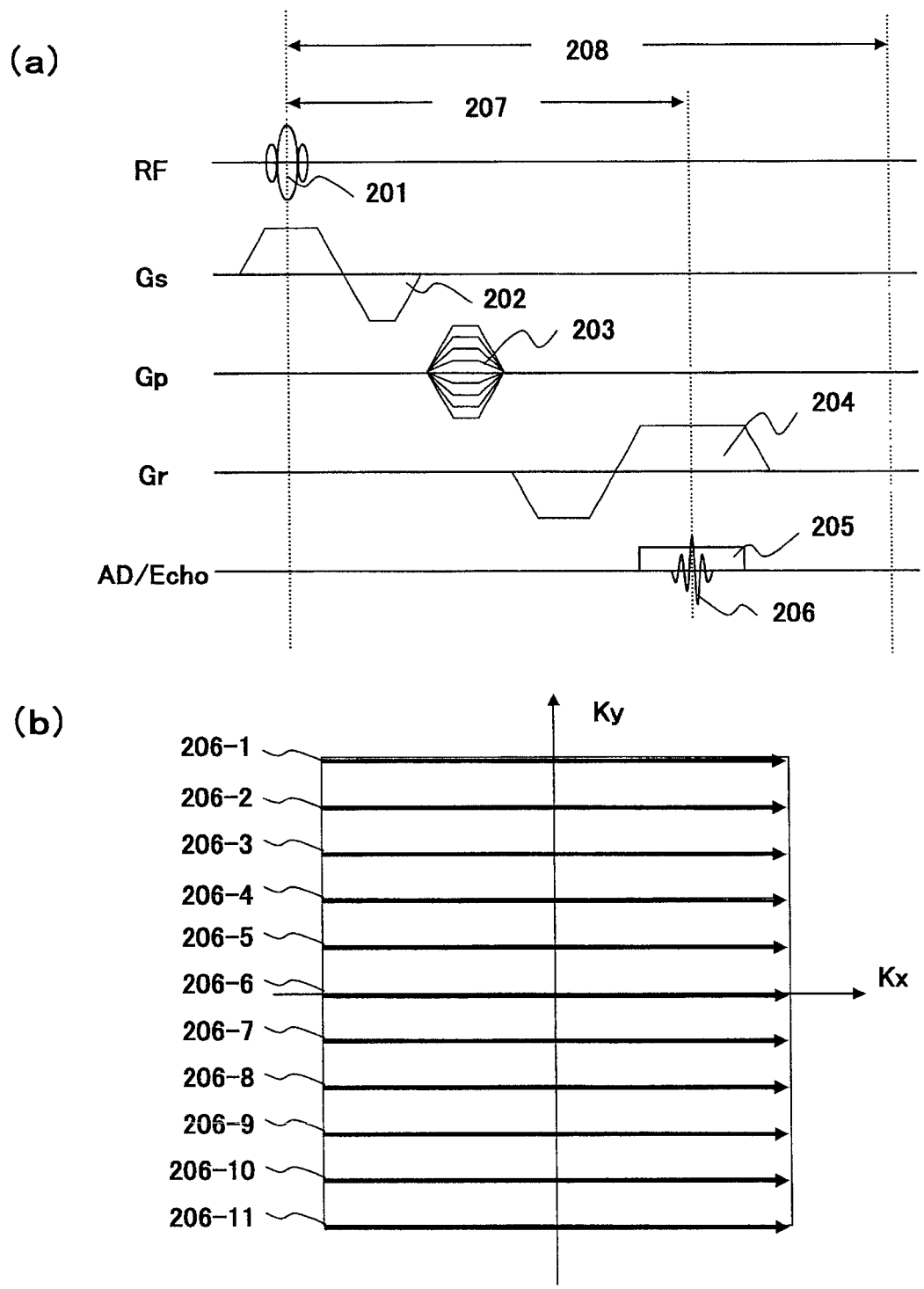
FIG. 10 illustrates one example of the pulse sequence employed in a conventional moving table imaging.
Figure 11:
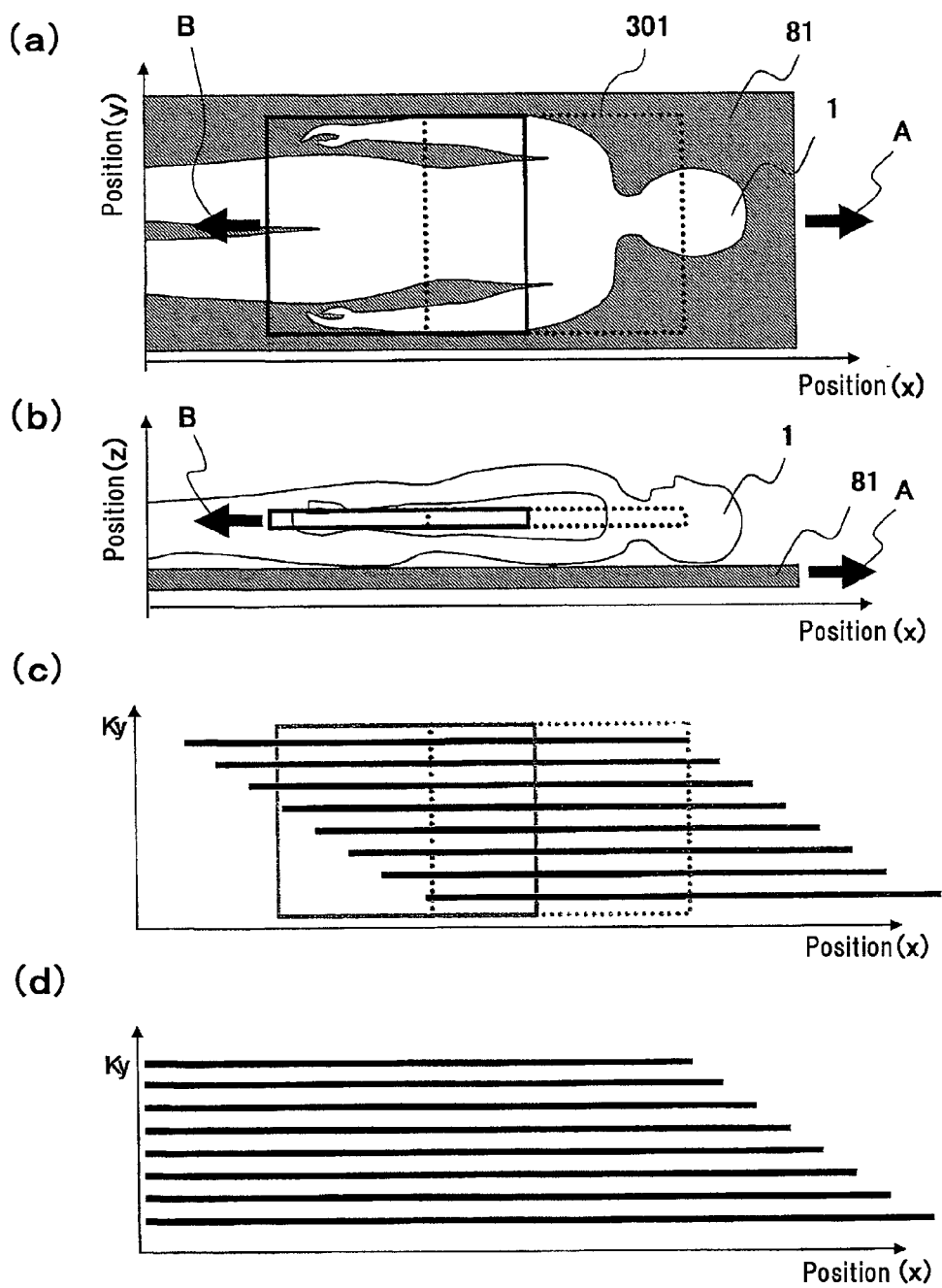
FIG. 11 illustrates the conventional moving table imaging.
Figure 12:
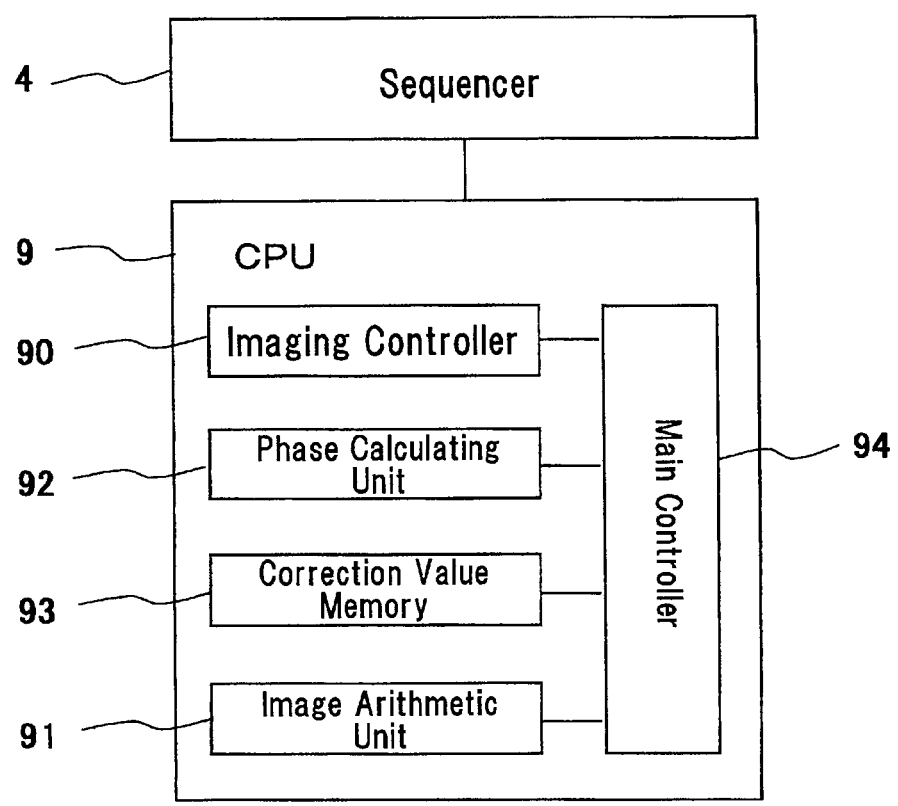
FIG. 12 illustrates a configuration example of the signal processing unit (CPU) of the present invention.

1. SUBJECT
2. STATIC MAGNETIC FIELD GENERATION SYSTEM
3. GRADIENT MAGNETIC FIELD GENERATION SYSTEM
4. SEQUENCER
5. SENDING SYSTEM
6. RECEIVING SYSTEM
7. SIGNAL PROCESSING SYSTEM
8. TABLE DRIVING SYSTEM
9. CENTRAL PROCESSING UNIT

What is claimed is:

1. A magnetic resonance imaging apparatus comprising:
a magnetic field generation system configured to generate each of a static magnetic field, an RF magnetic field, and a gradient magnetic field;
a transfer unit configured to move a subject at a moving velocity in a moving direction in the static magnetic field;
a signal processing system configured to measure a nuclear magnetic resonance signal generated from the subject and produce an image of the subject;
an imaging controller which controls the magnetic field generation system, the transfer unit and the signal processing system, and which executes, while moving the transfer unit continuously, an imaging sequence for measuring multiple nuclear magnetic resonance signals by applying multiple readout gradient magnetic fields, after applying RF pulse of one-time excitation; and
a phase calculation unit configured to calculate a phase difference produced by a positional deviation of the readout gradient magnetic fields between echoes, given to the multiple nuclear magnetic resonance signals, the positional deviation being caused by the continuous movement of the transfer unit, the moving direction being a readout gradient direction of the readout gradient magnetic fields, and the phase difference being calculated by using a value of readout gradient (Gr), application time of the readout gradient pulse ($\Delta t$), a signal acquisition interval (IET) and a positional shift ($\Delta x$) along the moving direction in the signal acquisition interval IET, wherein the phase calculation unit applies one of formula (5) and formula (5') to calculate the phase difference $\theta$:

$$\theta = \Delta\omega \times \Delta t \text{ MOD } 2\pi = (\gamma \times Gr \times \Delta x) \times \Delta t \text{ MOD } 2\pi \quad (5), \text{ and}$$

$$\theta(t) = \int \Delta\omega(t) dt \text{ MOD } 2\pi = \int [\gamma \times Gr \times \Delta x(t)] dt \text{ MOD } 2\pi \quad (5'),$$

where $\Delta\omega$ represents a difference in angular frequency caused by the positional deviation, and $\gamma$ represents a gyromagnetic ratio, the imaging controller corrects the phase difference calculated by the phase calculation unit.

2. The magnetic resonance imaging apparatus according to claim 1, wherein,
the imaging controller changes a parameter for executing the imaging sequence, and corrects the positional deviation.

3. The magnetic resonance imaging apparatus according to claim 1, wherein,
the imaging controller corrects the positional deviation as to each of the multiple nuclear magnetic resonance signals.

4. The magnetic resonance imaging apparatus according to claim 1, wherein,
the phase calculation unit calculates a correction value for correcting the positional deviation of the readout gradient magnetic fields based on a velocity of the transfer unit and measuring intervals of the multiple nuclear magnetic resonance signals.

5. The magnetic resonance imaging apparatus according to claim 1, wherein
the imaging controller executes a correction data acquisition sequence that has a sequence form being the same as the imaging sequence and does not include application of a phase encoding gradient pulse, and
the phase calculation unit calculates a correction value for correcting the positional deviation of the readout gradient magnetic fields, based on the nuclear magnetic resonance signals obtained in the correction data acquisition sequence.

6. The magnetic resonance imaging apparatus according to claim 2, wherein,
the imaging controller corrects a reference frequency that is used for measuring the nuclear magnetic resonance signals in accordance with a variation of the readout gradient magnetic field.

7. The magnetic resonance imaging apparatus according to claim 2, wherein
the imaging controller corrects an offset value of the static magnetic field in accordance with a variation of the readout gradient magnetic field.

8. The magnetic resonance imaging apparatus according to claim 3, wherein,
the imaging controller corrects a phase change of the nuclear magnetic resonance signals, the phase change being generated by a variation of the readout gradient magnetic fields.

9. The magnetic resonance imaging apparatus according to claim 1, wherein,
the imaging sequence is an imaging sequence according to echo planar method.

10. The magnetic resonance imaging apparatus according to claim 9, wherein
the imaging controller executes a correction data acquisition sequence while the table is brought to a halt, the sequence having a form being the same as the imaging sequence and not including application of a phase encoding gradient pulse, and the imaging controller creates a phase correction value based on the nuclear magnetic resonance signals obtained in the correction data acquisition sequence, and by using the phase correction value, the imaging controller corrects a phase error that occurs on odd-numbered signals and a phase error that occurs on even-numbered signals out of the multiple nuclear magnetic resonance signal.

11. The magnetic resonance imaging apparatus according to claim 1, wherein,
the imaging sequence is an imaging sequence according to fast spin echo method.

12. The magnetic resonance imaging apparatus according to claim 9, wherein the imaging sequence is a multi-shot imaging sequence for acquiring data of all phase encoding by more than once excitations, and the imaging controller controls the order for measuring signals so that the order for measuring signals is serial in a phase encoding direction.

13. The magnetic resonance imaging apparatus according to claim 9, wherein
the imaging sequence is an imaging sequence according to 3D echo planar method including phase encoding of a first axis and phase encoding of a second axis, and the imaging controller controls a measuring sequence so that the all phase encoding signals of another axis are acquired by one-time excitation, as to the phase encoding either of the first axis and the second axis, which are in the direction orthogonal to the moving direction of the transfer unit.

14. The magnetic resonance imaging apparatus of claim 1, wherein the imaging controller executes, while moving the transfer unit, 3D imaging sequence for measuring multiple nuclear magnetic resonance signals, by applying a phase encoding gradient magnetic field of a first axis, simultaneously with applying the phase encoding gradient magnetic field of a second axis and multiple readout magnetic fields, after one-time excitation RF pulse, and the imaging controller controls a measuring order so that all the phasing encoding signals being encoded by the phase encoding gradient magnetic field of the second axis are acquired at one-time excitation.

15. The magnetic resonance imaging apparatus according to claim 14, wherein,
the phase encoding of the second axis is a slice encoding.

16. The magnetic resonance imaging apparatus according to claim 14, wherein
the imaging controller controls the measuring sequence so that all the phase encoding signals are acquired at one-time excitation, as to one of the phase encoding of the first axis and the phase encoding of the second axis, the one having an encoding number smaller than an encoding number of another.

* * * * *